United States Patent
Sy et al.

(10) Patent No.: US 6,388,155 B1
(45) Date of Patent: May 14, 2002

(54) STYRENE DEHYDROGENATION REACTOR EFFLUENT TREATMENT

(75) Inventors: Angel S. Sy, Katy; Gautam M. Phanse, Houston, both of TX (US)

(73) Assignee: ABB Lummus Global Inc., Bloomfield, NJ (US)

( * ) Notice: Subject to any disclaimer, the term of this patent is extended or adjusted under 35 U.S.C. 154(b) by 0 days.

(21) Appl. No.: 09/630,656

(22) Filed: Aug. 1, 2000

(51) Int. Cl.⁷ ................................................ C07C 5/333
(52) U.S. Cl. ...................... 585/441; 585/435; 585/440; 585/950
(58) Field of Search ............................... 585/435, 440, 585/441, 950

(56) References Cited

U.S. PATENT DOCUMENTS

| | | | | |
|---|---|---|---|---|
| 3,256,355 A | * | 6/1966 | Gilman et al. ............... | 585/451 |
| 3,336,414 A | * | 8/1967 | Woerner ...................... | 585/800 |
| 3,412,171 A | * | 11/1968 | Welch et al. ................ | 585/621 |
| 3,728,413 A | * | 4/1973 | Woerner ...................... | 585/621 |
| 4,288,234 A | * | 9/1981 | Cox et al. ..................... | 95/207 |
| 4,628,136 A | | 12/1986 | Sardina ....................... | 585/441 |

\* cited by examiner

*Primary Examiner*—Walter D. Griffin
(74) *Attorney, Agent, or Firm*—Alix, Yale & Ristas, LLP

(57) ABSTRACT

The fouling in a styrene production process involving the dehydrogenation of ethylbenzene is reduced by removing polymerizable components of the gaseous dehydrogenation effluent prior to the condensation of the effluent in the main condenser system. This involves the scrubbing of the gaseous effluent with organic condensate from the main condenser system to remove styrene, divinylbenzene and other polymer precursors which may be present and sometimes some of the ethylbenzene. The scrubber may include a reboiler and stripping section and function as a full fractionator thereby reducing the need for downstream distillation.

7 Claims, 5 Drawing Sheets

STYRENE DEHYDROGENATION REACTOR EFFLUENT TREATMENT

FIELD OF THE INVENTION

This invention relates to a process for the production of styrene by the dehydrogenation of ethylbenzene in the presence of steam and more particularly to a method of reducing the fouling of certain process components due to polymer formation.

BACKGROUND OF THE INVENTION

In styrene manufacturing processes, many plants experience troublesome fouling and even plugging problems in certain equipment and particularly in the main condenser system, off-gas compressor and downstream cooler and lean oil scrubber/stripper system. This polymer formation is mainly due to the presence of uninhibited styrene and in many cases is aggravated by the presence of small concentrations of divinylbenzene and other polymer precursors produced along with styrene in the dehydrogenation reactor as a side reaction and also as a product of the dehydrogenation of diethylbenzene which may be present in the feed.

SUMMARY OF THE INVENTION

The invention relates to the reduction or elimination of the fouling in a styrene production process by removing polymerizable materials from the process stream upstream of the process components subject to fouling. More particularly, the invention relates to the scrubbing/prefractionation of the dehydrogenation effluent to remove divinylbenzene and styrene prior to the condensing of the effluent in the main condenser system with the scrubber/prefractionation being refluxed by organic condensate from the main condenser system. Alternately, the scrubber may include a reboiler and a stripping section and function as a full fractionator thereby reducing or eliminating the need for downstream distillation equipment and systems.

DESCRIPTION OF THE PREFERRED EMBODIMENTS

Figure 1:
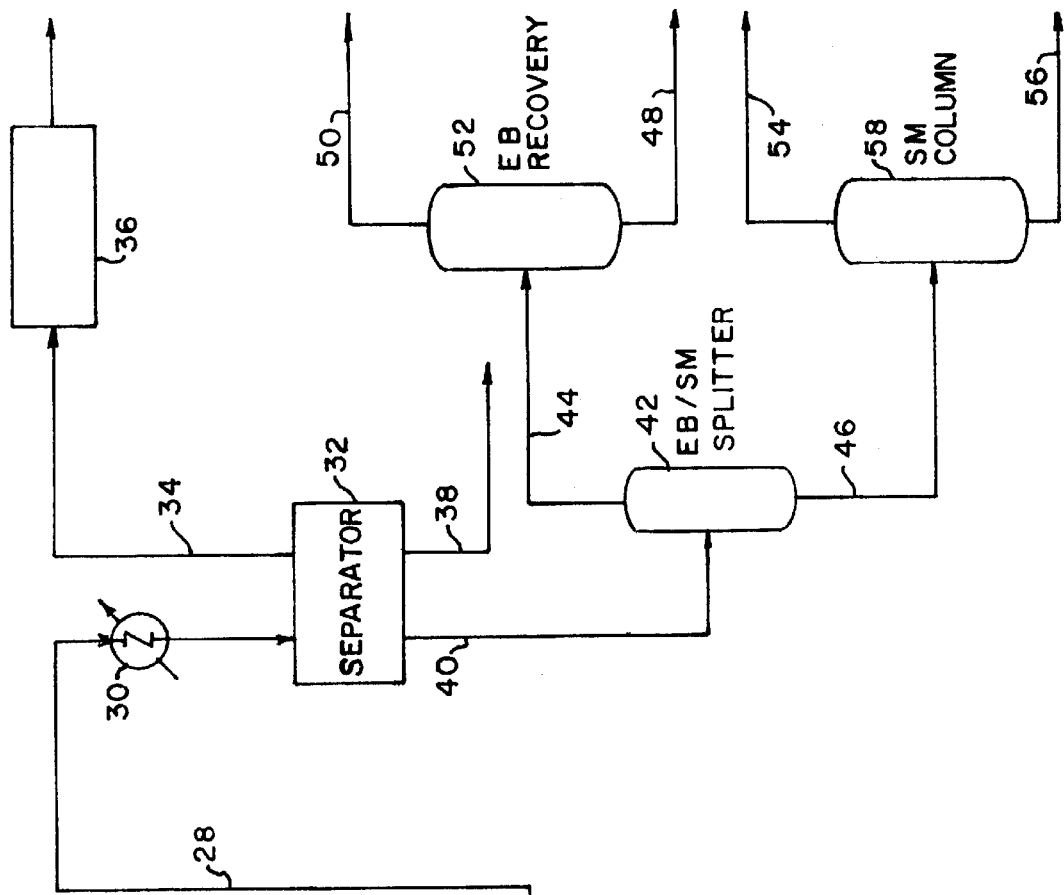
FIG. 1 is a process flow diagram of a prior art styrene production process involving the dehydrogenation of ethylbenzene.

The present commercial process for the production of styrene comprises the dehydrogenation of ethylbenzene using a conventional catalyst for this purpose such as iron oxide and using conventional, known operating conditions. Typically, the dehydrogenation is carried out at 600° C. or higher using low pressure and dilution steam. FIG. 1 of the drawings generally illustrates such a prior art process flow diagram. A steam superheater 10 produces a major portion of the diluent steam 12 for the process at a steam temperature above the dehydrogenation temperature. The ethylbenzene feed 14 is vaporized in the vaporizer/reboiler 16 and passed to the ethylbenzene separator drum 18 where vapor and liquid are separated and the liquid 20 recycled to the vaporizer/reboiler 16. The ethylbenzene vapor 22 is further heated in the waste heat exchanger 24 and fed to a conventional catalytic dehydrogenation reactor 26 along with the superheated diluent steam 12. The effluent gas 28 from the dehydrogenation reactor 26 contains primarily styrene, hydrogen, unreacted ethylbenzene, divinylbenzene and small amounts of benzene, toluene, methane, ethane, carbon monoxide, carbon dioxide, various polymeric materials and tars as well as an aqueous component. The effluent gas 28 is partially cooled in the waste heat exchanger 28 against the incoming ethylbenzene and sometimes against other streams and then fed to the main condenser 30. The styrene, unreacted ethylbenzene, divinylbenzene, polymeric materials, tars and the aqueous component are condensed while the hydrogen, methane, ethane and carbon monoxide and dioxide and most of the benzene and toluene remain in the gaseous phase. From the main condenser 30, the now partially condensed effluent is fed to the phase separator 32. The gaseous phase 34 is separated and treated by means including compression 36 followed by recovery of the benzene and toluene.

Also separated in the phase separator 32 is the aqueous phase 38, which will normally be treated in a condensate stripper (not shown). The organic dehydrogenation mixture 40 from the separator 32 comprises primarily the crude styrene and the unreacted ethylbenzene which are fed to the distillation column 42 which is often referred to as an ethylbenzene/styrene monomer splitter. This distillation may be in a single column or a plurality of columns in series. The key separation is between the ethylbenzene and lighter materials 44 and the styrene and heaver materials 46. The column is operated at reduced pressure to lower the distillation temperature and thereby reduce styrene polymerization. The ethylbenzene 48 is separated from the lighter materials 50 in the ethylbenzene recovery distillation column 52 and the ethylbenzene 48 is recycled. The styrene monomer product 54 is separated from the heavier materials 56, primarily tar, in the styrene monomer recovery distillation column 58.

The problem encountered with these prior art systems such as shown in FIG. 1 and described above is that polymers can form primarily in the main condenser 30 and all downstream equipment including the off-gas compressor 36. This polymer formation is due to the presence of uninhibited styrene and aggravated by the likely presence of small concentrations of divinylbenzene and other polymer precursors produced along with styrene in the dehydrogenation reactor as a side reaction and/or as a product of the dehydrogenation of diethylbenzene which may be present in the feed.

Figure 2:
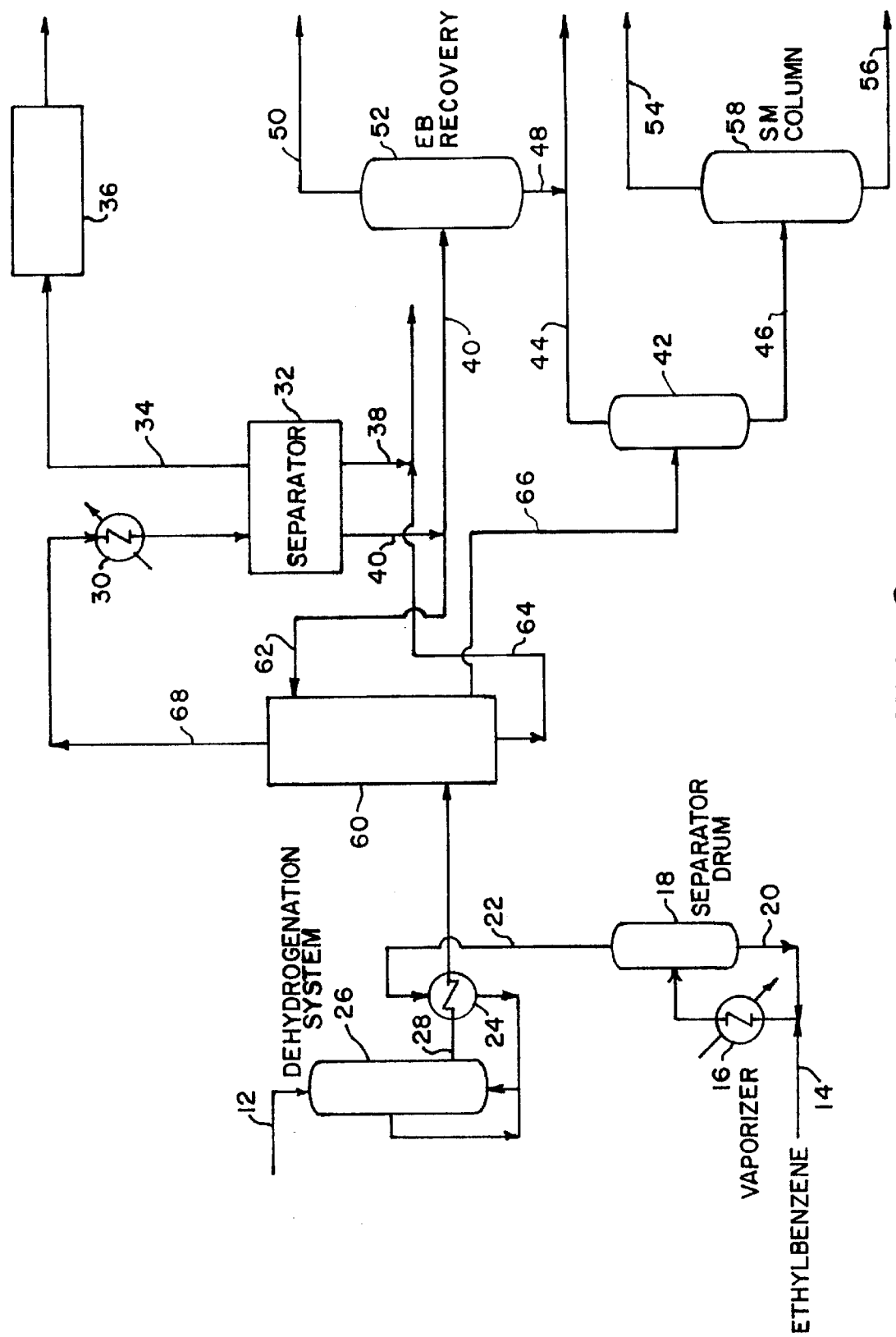
FIG. 2 is a styrene production process flow diagram incorporating the scrubbing/prefractionating of the present invention.

One embodiment of the present invention is shown in FIG. 2. In this embodiment, a scrubber 60 is added and the effluent gases 28 from the dehydrogenation reactor 26 are fed to the lower end of this scrubber. The scrubber may be any type of liquid/gas contactor such as a packed bed column. Fed into the top of the scrubber 60 is reflux 62 which comprises a portion of the organic dehydrogenation mixture 40 from the phase separator 32. Scrubbing with this organic dehydrogenation mixture scrubs a significant amount of the styrene and divinylbenzene from the dehydrogenation effluent gases 18 and also forms a condensate aqueous phase. The aqueous phase is removed at 64 and either sent to separator 32 or combined with the aqueous phase 38 from the phase separator 32 for subsequent treatment as shown. Depending on the operating conditions chosen, the amount of aqueous phase formed in the scrubber will vary and in some cases may be totally avoided. In other cases, intermediate side draws from the scrubber can be used to withdraw the aqueous phase. The organic phase 66 from the scrubber 60 is fed to the distillation column 42 for separation of the ethylbenzene and styrene monomer. The overhead 44 from the distillation column 42 is relatively pure ethylbenzene which is combined with the ethylbenzene 48 from the ethylbenzene distillation column 52 for direct recycle. The styrene monomer stream 46 from the distillation column 42 is processed as in FIG. 1 in the distillation column 58. The remaining overhead gases 68 from the scrubber 60 are fed to the main condenser just as in FIG. 1.

In the invention shown in FIG. 2, most of the divinylbenzene and most of the styrene monomer are removed from the gaseous dehydrogenation effluent before feeding this gaseous effluent to the main condenser 30. Removing most of these two materials eliminates the fouling and plugging problems in the main condenser 30 and the off-gas compressor 36 as well as the other downstream equipment and piping. An added advantage is that there is a partial separation in the scrubber 60 between the ethylbenzene and the styrene monomer. This permits a reduction in the size and duty of the ethylbenzene/styrene monomer splitter or distillation column 42 and in the size and duty of the ethylbenzene recovery distillation column 52. A further advantage is that there is a drastic reduction in the styrene monomer concentration in the organic liquid in contact with the aqueous condensate in the separator 32 from over 60% to less than 2% which will tend to alleviate polymer fouling in the downstream condensate stripper system.

Another advantage is the absence of lights such as benzene, toluene and dissolved gases such as $CO_2$ in the feed to the ethylbenzene/styrene splitter distillation column 42. This permits a higher temperature and increased driving force for the azeotropic boiler/condenser of the distillation column 42 to either reduce the surface requirement or reduce the operating pressure. Reducing the pressure would be another factor in reducing polymer formation in the column. Also, corrosion problems in the overhead system are reduced due to the absence of carbon dioxide.

Computer simulations of refluxed scrubber 60 indicate that about one quarter to one half of the ethylbenzene content of the dehydrogenation effluent 28 is prefractionated from styrene monomer in the scrubber 60 and the styrene content of the overhead 68 is reduced to less than 2 wt. % without any external heat source for the scrubber. As a result, the reboiler duty for the ethylbenzene/styrene monomer splitter 42 and the ethylbenzene recovery column are reduced significantly.

Figure 3:
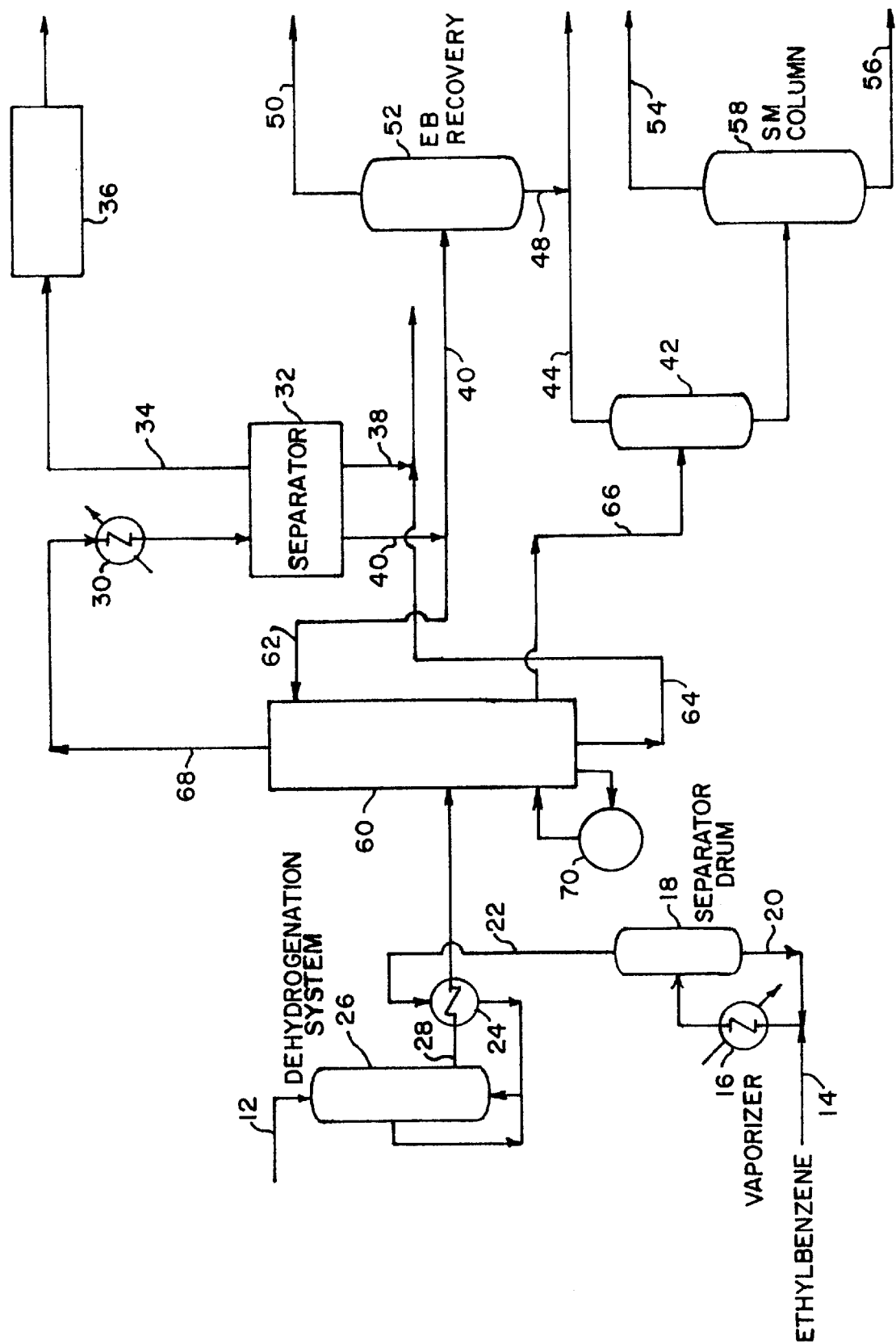
FIGS. 3, 4 and 5 are process flow diagrams similar to FIG. 2 but illustrating modified embodiments of the invention.
Figure 4:
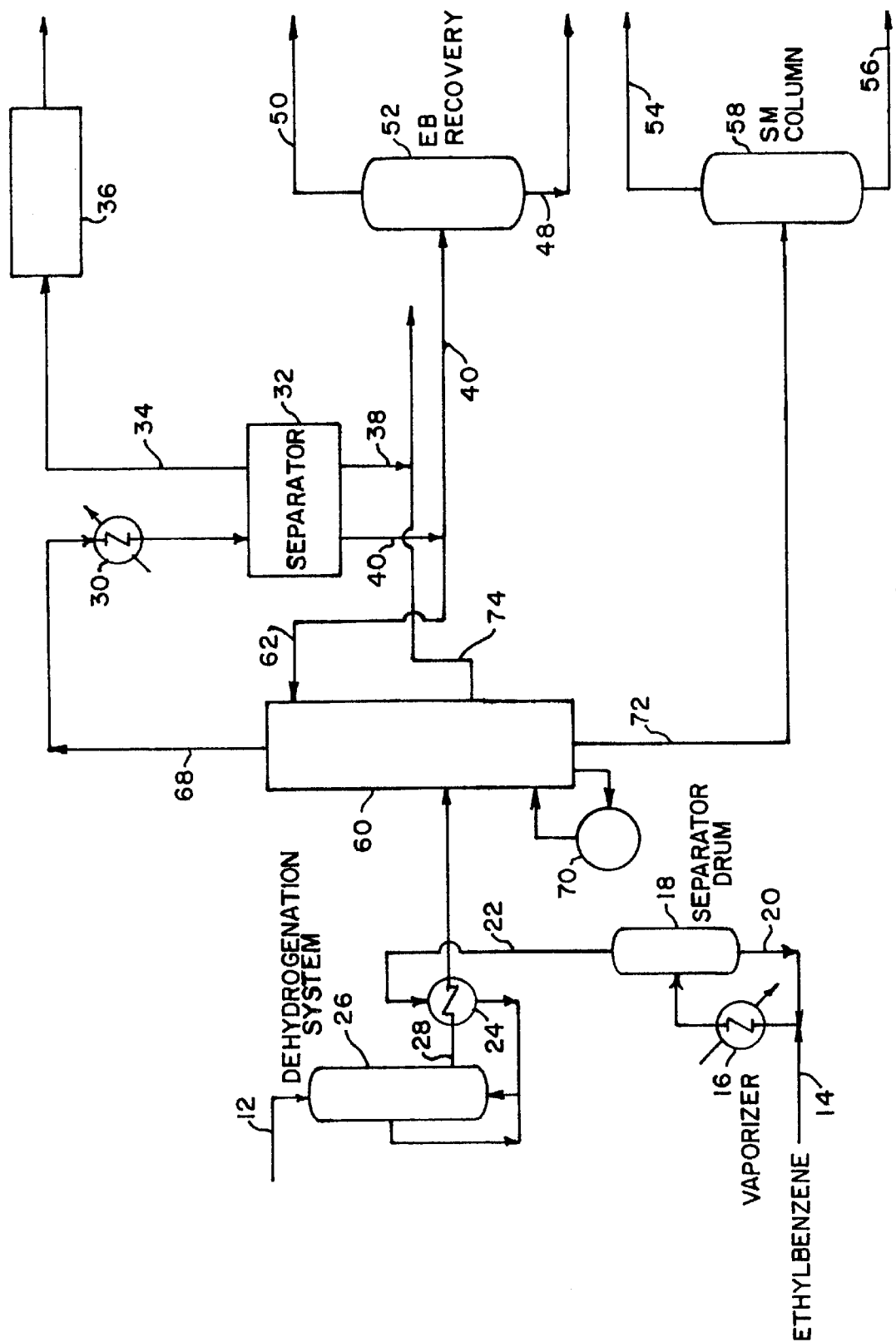

Another embodiment of the invention is shown in FIG. 3 in which a stripping section with a reboiler 70 is added to the bottom of the refluxed scrubber 60. This serves to further fractionate ethylbenzene and lighter from styrene monomer and heavier to further reduce the reboiler duty of the ethylbenzene/styrene monomer splitter 42. FIG. 4 illustrates a variation of this embodiment in which the size and duty of the reboiler 70 and the stripping section of the scrubber 60 are increased to the extent that there is a complete separation of ethylbenzene and styrene monomer thereby completely eliminating the need for a ethylbenzene/styrene monomer splitter. In this case, the bottoms 72 from the scrubber 60 are fed directly to the styrene monomer recovery distillation column 58 while the aqueous side stream 74 is combined with the aqueous phase 38 from the phase separation 32.

Figure 5:
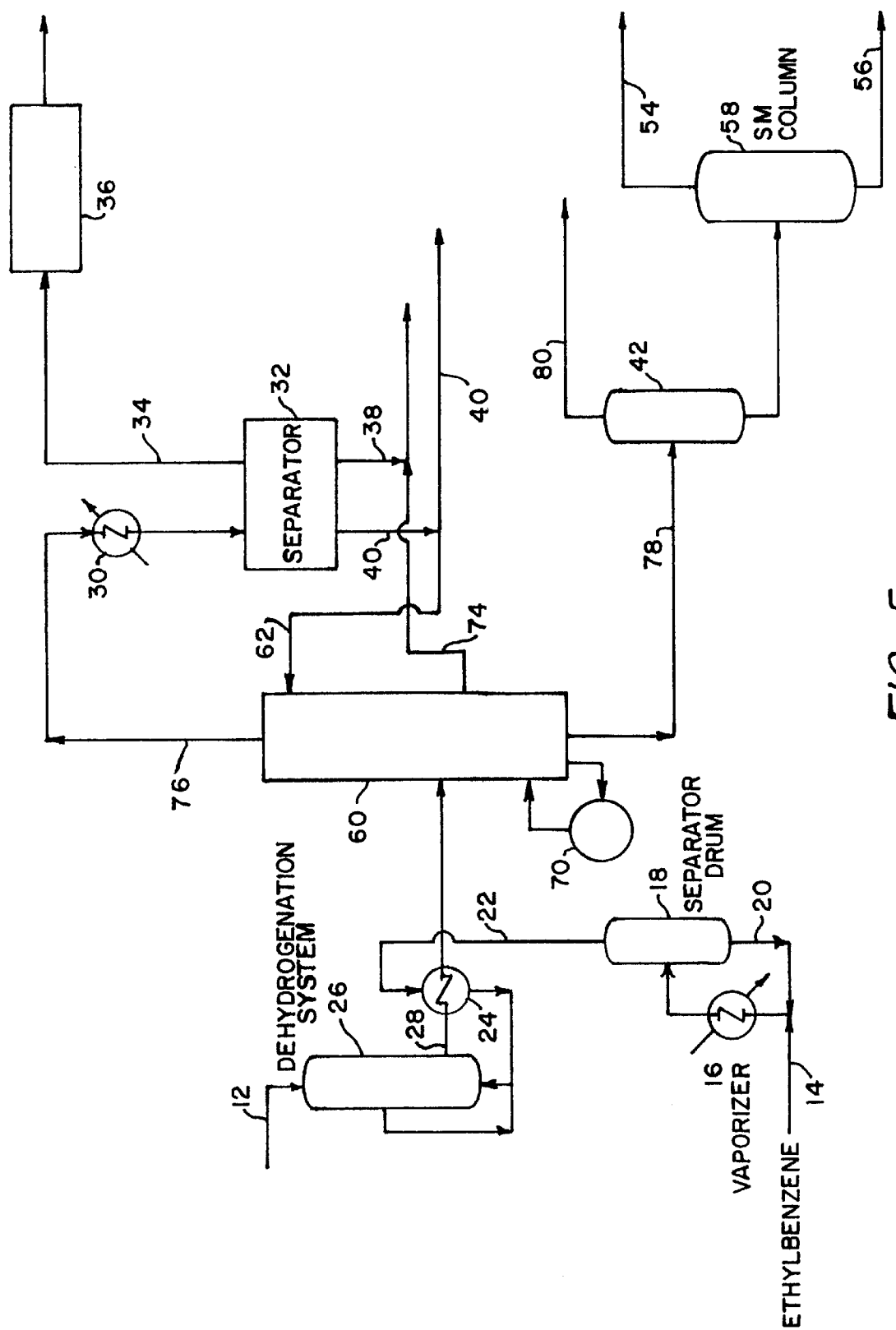

A further embodiment of the invention is illustrated in FIG. 5 in which the primary separation in the scrubber 60 is between the toluene and lighter as overhead, now designated 76, and the ethylbenzene and heavier as bottoms, now designated 78. The bottoms 78 now contain essentially all of the ethylbenzene which is separated as the overhead stream, now designated 80, from the ethylbenzene/styrene monomer splitter 42. This completely eliminates the need for an ethylbenzene recovery distillation column 52 as included in the previous embodiments.

What is claimed is:

1. A process for the production of styrene monomer from ethylbenzene comprising the steps of:
   a. catalytically dehydrogenating said ethylbenzene in the presence of steam thereby catalytically producing a dehydrogenation effluent gas containing unreacted ethylbenzene and lighter components and styrene monomer and heavier components;
   b. scrubbing said effluent gas with reflux to remove at least a portion of said styrene monomer and heavier components from said effluent gas;
   c. condensing a portion of said scrubbed effluent gas thereby producing a liquid organic dehydrogenation mixture; and
   d. using a portion of said liquid organic dehydrogenation mixture as said reflux for said step of scrubbing.

2. In a process as recited in claim 1 wherein said step of scrubbing styrene monomer from said effluent gas includes the step of scrubbing at least a portion of said ethylbenzene from said effluent gas.

3. In a process as recited in claim 1 wherein said step of scrubbing further includes the step of fractionating.

4. In a process as recited in claim 3 wherein said step of fractionating comprises the step of separating at least a portion of said ethylbenzene and lighter components as overhead from said styrene monomer.

5. In a process as recited in claim 3 wherein said step of fractionating comprises the step of separating essentially all of said ethylbenzene and lighter components as overhead from said styrene monomer.

6. In a process as recited in claim 3 wherein said effluent gas contains toluene and wherein said step of fractionating comprises the step of separating said toluene and lighter components as overhead from said ethylbenzene and styrene monomer.

7. A process as recited in claim 1 wherein said effluent gas further contains divinylbenzene and wherein said step of scrubbing further comprises scrubbing at least a portion of said ethylbenzene and at least a portion of said divinylbenzene from said effluent gas.

* * * * *